United States Patent
Shao et al.

(10) Patent No.: US 10,905,735 B2
(45) Date of Patent: Feb. 2, 2021

(54) **CHEMOSYNTHETIC CYCLO-HEPTA MODIFIED PEPTIDE CAPABLE OF INHIBITING TOXIN OF *STAPHYLOCOCCUS AUREUS* AND USE THEREOF**

(71) Applicant: ZHONGCHENG INVESTMENT MANAGEMENT (SHANGHAI) CO., LTD, Shanghai (CN)

(72) Inventors: Ningsheng Shao, Beijing (CN); Guang Yang, Beijing (CN); Liangyou Wang, Suzhou (CN); Hongmei Ding, Beijing (CN); Yaping Gao, Beijing (CN); Shaohua Li, Beijing (CN); Hui Li, Beijing (CN); Jie Li, Beijing (CN); Jie Dong, Beijing (CN); Wenhui Xia, Haikou (CN); Xiaoping Liang, Haikou (CN)

(73) Assignee: ZHONGCHENG INVESTMENT MANAGEMENT (SHANGHAI) CO., LTD, Shanghai (CN)

( * ) Notice: Subject to any disclaimer, the term of this patent is extended or adjusted under 35 U.S.C. 154(b) by 0 days.

(21) Appl. No.: 16/097,964

(22) PCT Filed: Apr. 27, 2017

(86) PCT No.: PCT/CN2017/082106
§ 371 (c)(1),
(2) Date: Oct. 31, 2018

(87) PCT Pub. No.: WO2017/190619
PCT Pub. Date: Nov. 9, 2017

(65) Prior Publication Data
US 2019/0142892 A1    May 16, 2019

(30) Foreign Application Priority Data

May 3, 2016    (CN) .......................... 2016 1 0284547

(51) Int. Cl.
| A61K 38/02 | (2006.01) |
| C07K 7/08 | (2006.01) |
| A61P 31/04 | (2006.01) |
| A61K 38/12 | (2006.01) |

(52) U.S. Cl.
CPC .............. *A61K 38/02* (2013.01); *A61K 38/12* (2013.01); *A61P 31/04* (2018.01); *C07K 7/08* (2013.01)

(58) Field of Classification Search
CPC ........... C07K 7/08; A61P 31/04; A61K 38/02; A61K 38/12
See application file for complete search history.

(56) References Cited

U.S. PATENT DOCUMENTS

| 2007/0071768 A1 | 3/2007 | Balaban |
| 2007/0092575 A1 | 4/2007 | Balaban et al. |

FOREIGN PATENT DOCUMENTS

| CN | 1394871 A | 2/2003 |
| CN | 1569889 A | 1/2005 |
| CN | 1724566 A | 1/2006 |
| CN | 104072579 A | 10/2014 |
| WO | 2005007684 A1 | 1/2005 |
| WO | 2005007685 A1 | 1/2005 |
| WO | 2006107945 A2 | 10/2006 |
| WO | 2006122127 A1 | 11/2006 |

OTHER PUBLICATIONS

International Search Report for PCT/CN2017/082106 dated Jul. 21, 2017 and its English translation provided by WIPO.
Written Opinion of the International Search Authority PCT/CN2017/082106 dated Jul. 21, 2017 and its English translation provided by Google Translate.

*Primary Examiner* — Li N Komatsu
(74) *Attorney, Agent, or Firm* — Ladas & Parry, LLP

(57) ABSTRACT

The invention relates to a chemosynthetic cyclo-hepta modified peptide capable of inhibiting toxins of *Staphylococcus aureus* and a use thereof. The chemosynthetic peptide can specifically inhibit production of the toxins of *Staphylococcus aureus* by means of the binding of the RNAIII activator protein by a *Staphylococcus aureus* autocrine. The invention also relates to the use of the chemosynthetic peptide in the pharmaceutical field. The sequence general formula of the chemosynthetic cyclo-hepta modified peptide is $CH_3-(CH_2)m-X-G-(CQHWWHWYC)-(R)n-Y$. The results show that the modified peptide can be dissolved well in water and has good activity against the toxins of *Staphylococcus aureus*.

9 Claims, 3 Drawing Sheets

Specification includes a Sequence Listing.

SEQUENCE LISTING

<160> NUMBER OF SEQ ID NOS: 1

<210> SEQ ID NO 1
<211> LENGTH: 9
<212> TYPE: PRT
<213> ORGANISM: Artificial Sequence
<220> FEATURE:
<223> OTHER INFORMATION: Chemically synthesized as mentioned in
      application document

<400> SEQUENCE: 1

Cys  Gln  His  Trp  Trp  His  Trp  Tyr  Cys
1                   5

CHEMOSYNTHETIC CYCLO-HEPTA MODIFIED PEPTIDE CAPABLE OF INHIBITING TOXIN OF *STAPHYLOCOCCUS AUREUS* AND USE THEREOF

CROSS-REFERENCE TO RELATED APPLICATIONS

The present application is the U.S. National Phase of PCT/CN2017/082106 filed on Apr. 27, 2017 which claims priority to the Chinese patent application No. 201610284547.8, filed on May 3, 2016, the disclosures of which are incorporated herein by reference in their entireties.

FIELD OF THE INVENTION

The present invention relates to a chemosynthetic cyclo-hepta modified peptide capable of inhibiting the toxins of *Staphylococcus aureus* and a use thereof. The chemosynthetic peptide can specifically inhibit production of the toxins of *Staphylococcus aureus* by means of the binding of the RNAIII activator protein by a *Staphylococcus aureus* autocrine. The invention also relates to the use of the chemosynthetic peptide in the pharmaceutical field.

BACKGROUND OF THE INVENTION

*Staphylococcus aureus* is a common gram-positive pathogen, which is one of the main microorganisms that cause fatal diseases such as burn and war wound infection, pneumonia, endocarditis, septicemia, toxic shock and so on. The number of people infected with *Staphylococcus aureus* in hospitals only exceeds millions a year. At present, the treatment of *Staphylococcus aureus* is mostly combination of antibiotics, but the effect is not satisfactory. Because *Staphylococcus aureus* is susceptible to drug resistance, which has no good solution, many common antibiotics are ineffective to it. Controlling *Staphylococcus aureus* infection is one of the problems to be solved in clinical medicine.

The main pathogenic substances of *Staphylococcus aureus* are toxins including hemolytic toxins, leukocides and enterotoxins. The lastest studies show that the synthesis of these virulence factors in *Staphylococcus aureus* is controlled by an adjustable RNA molecule and RNAIII. RNAIII activates the gene transcription of virulence factors and regulates the translation of virulence factors through base complementation. In the early logarithmic growth phase of bacteria, the level of RNAIII is low, but in the late logarithmic phase growth phase, the level of RNAIII increases by 40 times. The level of RNAIII is regulated by the protein secreted by *Staphylococcus aureus* itself and RNAIII activating protein (RAP), so the factor RAP is also called *Staphylococcus aureus* virulence stimulator. *Staphylococcus aureus* secretes RAP continuously and activates virulence factor only after RAP reaches a certain concentration. *Staphylococcus aureus* itself is not pathogenic without RAP. In 1998, the research result published by Balaban et al. in the journal Science show that by immunizing animals with RAP prepared, the antibody can effectively protect mice from the infection with *Staphylococcus aureus* (Balaban N, et al. Autoinducer of virulence as a target for vaccine and therapy against *Staphylococcus aureus*. Science, 1998, 280(17):438-440).

Using phage display technique, the inventor screened the small molecular cyclo-heptapeptide MRK (CQHWWHWYC, SEQ ID NO: 1), which can specifically bind to RAP molecule and inhibit its activity, from the random cyclo-heptapeptide library, please refer to CNO315020.5 and other previous work. In vitro and in vivo experiments show that the small peptide may inhibit the production of the toxins of *Staphylococcus aureus*. However, in the subsequent studies, the inventor found that the small peptide has a major defect-insoluble in water or physiological solution, only soluble in organic solvents (such as DMSO), which seriously affects its bioactivity and makes the small peptide unusable in clinic. For this reason, this has become a major problem troubling inventor, so that research and development work cannot be advanced. After repeated screening experiments, the inventor tried various structural modification methods, including the introduction of hydrophilic groups such as PEG, nanocrystallization by nanotechnology, and even the use of liposome or micelle drug loading, but these methods have little effect, even greatly affect the activity and stability of cyclo-heptapeptide. In addition, in recent years, in the field of enzyme, protein and peptide pharmaceuticals, there have been a number of reports on chemical modifications, such as improved stability and long-lasting effects (2012-2013 Development Report on Biochemistry and Molecular Biology, China Science and Technology Press, 2014.04), but what kind of chemical modification is useful remains complicated due to different function and structure, and needs to be determined according to specific situation.

SUMMARY OF THE INVENTION

The invention relates to the chemical modification of cyclo-heptapeptide, belonging to a small molecular peptide. The main purpose of the invention is to improve water solubility and maintain biological activity. The small peptide is chemically modified on the basis of the cyclo-heptapeptide and the sequence general formula is $CH_3$—$(CH_2)$m-X-G-(CQHWWHWYC)—(R)n-Y. The results show that chemosynthetic cyclo-hepta modified peptide (abbreviated as MRG) not only can be dissolved well in water, but also has good activity against the toxins of *Staphylococcus aureus* compared with its original cyclo-heptapeptide, so that the above-mentioned technical problems are solved. Terminology: cyclo-heptapeptide refers to CQHWWHWYC (SEQ ID NO: 1), abbreviated as MRK.

The compound of the present invention is completely new in both source and structure, and has not been reported in any literature.

DETAILED DESCRIPTION OF THE INVENTION

The invention relates to a novel chemosynthetic cyclo-hepta modified peptide capable of inhibiting the toxins of *Staphylococcus aureus* and a preparation method thereof. The chemosynthetic peptide can specifically inhibit the production of the toxins of *Staphylococcus aureus*.

Another purpose of the invention is to provide the use of the chemosynthetic peptide in the pharmaceutical field.

The compound of the present invention is a small molecular polypeptide analogue (hereinafter referred to as "the peptide", "cyclo-hepta modified peptide") having the following general chemical structural formula:

$$CH_3\text{—}(CH_2)\text{m-X-G-(CQHWWHWYC)—(R)n-Y};$$

wherein, m=0-20, preferably 3-17, more preferably 6-14, most preferably 8-12;

X is selected from a group consisting of CO, NHCO, O or S, preferably X=CO;

n=1-10, preferably 1-7, more preferably 2-4, most preferably 3;

Y is selected from OH or $NH_2$;

G represents natural L-glycine residues or D-type isomers thereof;

C represents natural L-cysteine residues or D-isomers thereof, Q represents natural L-type glutamine residues or D-type isomers thereof, H represents histidine residues or D-type isomers thereof, W represents natural L-type tryptophan residues or D-type isomers thereof, Y represents natural L-tyrosine residues or D-type isomers thereof, R represents natural L-type arginine residues or D-type isomers thereof, and two cysteines represented by C are linked by a disulfide bond.

The peptide can specifically bind to the virulence stimulator RAP of *Staphylococcus aureus* and inhibit the production of the toxins of *Staphylococcus aureus*.

The peptide is synthesized by chemical synthesis. In other words, the peptide is obtained by chemical synthesis.

wherein $CH_3$—$(CH_2)_m$- represents the alkyl portion of the alkanoyl group, preferably $CH_3(CH_2)_{10}$-(m=10), which forms a lauroyl modified G when being linked to X=CO.

G, C, Q, H, W, Y, R independently represent the following groups: G represents natural L-glycine residues or D-type isomers thereof; C represents natural L-cysteine residues or D-type isomers thereof; Q represents natural L-glutamine residues or D-isomers thereof; H represents histidine residues or D-type isomers thereof; W represents natural L-tryptophan residues or D-type isomers thereof, Y represents natural L-tyrosine residues or D-type isomers thereof; R represents natural L-arginine residues or D-isomers thereof.

The two cysteines of the 9 amino acid sequences CQHWWHWYC (SEQ ID NO: 1) are linked by a disulfide bond.

A solid-phase synthesis method for preparing the peptide comprises the following steps:

Step 1, the conventional protected amino acids are coupled one by one with Rink Amide-AM Resin as the starting carrier, and the substitution degree sub is 0.45-0.55 mmol/g.

Step 2, under the action of the condensation reagents of 1-hydroxybenzotriazole (HOBT) and N,N'-diisopropyl carbodiimide (DIC), by using a solid-phase polypeptides stepwise condensation method, the amino acids protected by Fmoc are coupled one by one according to the sequence of the peptides from C to N terminals to obtain:
Gly-Cys(Trt)-Gln(Trt)-His(Trt)-D-Trp(Boc)-Trp(Boc)-His(Trt)-Trp(Boc)-Tyr(tBu)-Cys (Trt)-Arg(pbf)-Arg(pbf)-Arg(pbf)-Rink Amide-AM Resin.

Step 3, under the action of the condensation reagent of O-benzotriazole-N,N,N',N'-tetramethyl-uronium-hexafluorophosphate (HBTU) and N,N-diisopropyl ethylamine (DIPEA), dodecanoic acid is coupled to obtain:
$CH_3(CH_2)_{10}$CO-Gly-Cys(Trt)-Gln(Trt)-His(Tr)-D-Trp(Boc)-Trp(Boc)-His(Trt)-Trp(Boc)-Tyr(tBu)-Cys(Tr)-Arg(pbf)-Arg(pbf)-Arg(pbf)-Rink Amide-AM Resin.

Step 4, a conventional cracking reagent is mixed with the linear peptide resin obtained in step 3 to be subjected to cracking reaction, so as to remove Rink Amid-AM Resin and MRG side chain protection group, and then the MRG linear crude peptide is obtained by sedimentation, centrifugation, washing and drying.

Step 5, the linear crude peptide obtained in step 4 is grinded to powder, and the MRG linear crude peptide is dissolved in a mixed solution of pure water and acetonitrile (2:1) until the concentration is 1 mmol/500 mL, thus obtaining a linear crude peptide solution.

Step 6, diluted ammonia is dropwisely added to the MRG linear crude peptide solution to adjust the pH of the MRG linear crude peptide solution to 7.1-7.3, and stirred at a temperature of about 30° C. to be subjected to cyclization experiment. The cyclization time is 20-40 min. Whether the cyclization is complete is detected by high performance liquid chromatography (HPLC) and the cyclization is terminated by adding acetic acid to adjust pH to the acidic condition after the cyclization is complete.

Step 7, the target product crude product solution of step 6 is separated and purified by $C_{18}$ reversed-phase high performance liquid chromatography column, and the high purity product is obtained after rotary evaporateion and freeze-drying.

The invention also relates to the use of the peptide in the preparation of drugs against *Staphylococcus aureus* infection.

The chemosynthetic peptide with the above structure can specifically bind to the virulence stimulator RAP of *Staphylococcus aureus* and inhibit its activity.

The invention particularly relates to the peptide improving the solubility of the "cyclo-heptapeptide" (CQHWWHWYC) (SEQ ID NO: 1).

The main reason of resistance to antibiotics in traditional antibiotics therapy is that bacteria produce an inducible enzyme that decomposes effective groups of antibiotics under the pressure of survival. The invention utilizes the polypeptide compound specifically inhibiting RAP activity to establish a treatment scheme for *Staphylococcus aureus* infection, and finds a new outlet for the treatment of the common, recurrent and fatal drug-resistant *Staphylococcus aureus* infection which has been troubling the clinic.

The invention is of great significance to the development of novel small molecule peptide medicines resistant to *Staphylococcus aureus* infection, and has wide use value and broad market prospect.

EXAMPLES

Figure 1:
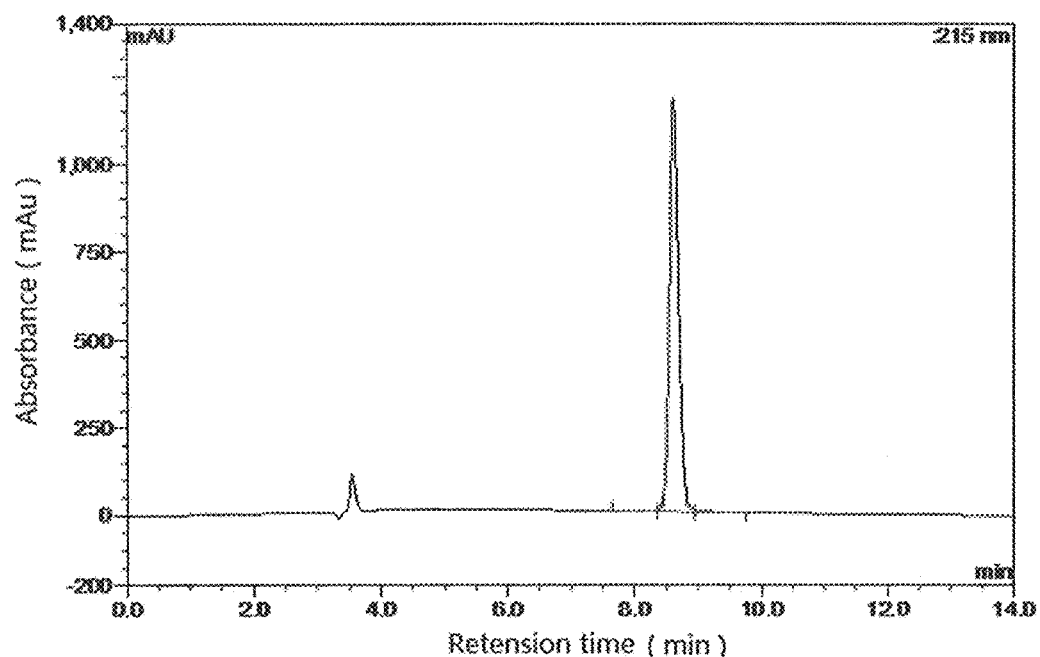
FIG. 1: HPLC purity identification chromatogram of chemosynthetic cyclo-heptapeptide MRK

The present invention is further described in detail by examples below.

Example 1: Preparation of Chemosynthetic Cyclo-Heptapeptide MRK by Solid Phase Synthesis 1. Synthetic Peptide Sequence: CQHWWHWYC (SEQ ID NO: 1) (End-to-End Ring Forming, Molecular weight 1346.5)

2. Synthesis Steps:

Step 1, raw materials needed for solid state synthesis H-Cys(Trt)-2-Chlorotrityl Resin(Shanghai Jier Biochemistry), Fmoc-Tyr(tBu)-OH, Fmoc-Trp-OH, Fmoc-His(Trt)-OH, Fmoc-Gln-OH, Fmoc-Cys(Trt)-OH, DCC, HOBt, TFAEDT, m-Cresol.

Step 2, solid state synthesis

Standard Fmoc-AA-OH/DCC/HOBt method 1.1 g H-Cys(Trt)-2-Chlorotrityl Resin (0.6 mmol) is used as the carrier, both amino acids and condensation agents are 3 times excessive, and 2.218 g Cys(Trt)-Gln-His(Trt)-Trp-Trp-His(Trt)-Trp-Tyr(tBu)-Cys(Trt)-2-Chlorotrityl Resin is obtained after synthesis.

Step 3, peptide resin cracking 210 mg crude product linear peptide is obtained with 0.5 g Cys(Trt)-Gln-His(Trt)-Trp-Trp-His(Trt)-Trp-Tyr(tBu)-Cys(Trt)-2-Chlorotrityl Resin, 0.1 mL m-Cresol, 0.3 mL EDT, 7.5 mL TFA reacting at 0° C. for 90 min.

Step 4, linear peptide oxidation 200 mg crude linear peptide is dissolved in 2000 mL water, pH is adjusted to 7-8 with $NaHCO_3$, $K_3Fe(CN)_6$ (2 mg/mL) solution is slowly dropwisely added to the reaction solution to show light yellow, and then the reaction continues for 1 hour. Cyclic peptide 76.7 mg (purity >95%) is obtained by solid phase extraction with $C_{18}$ column and elution with 80% acetonitrile solution.

Step 5, purification and structure confirmation

Figure 2:
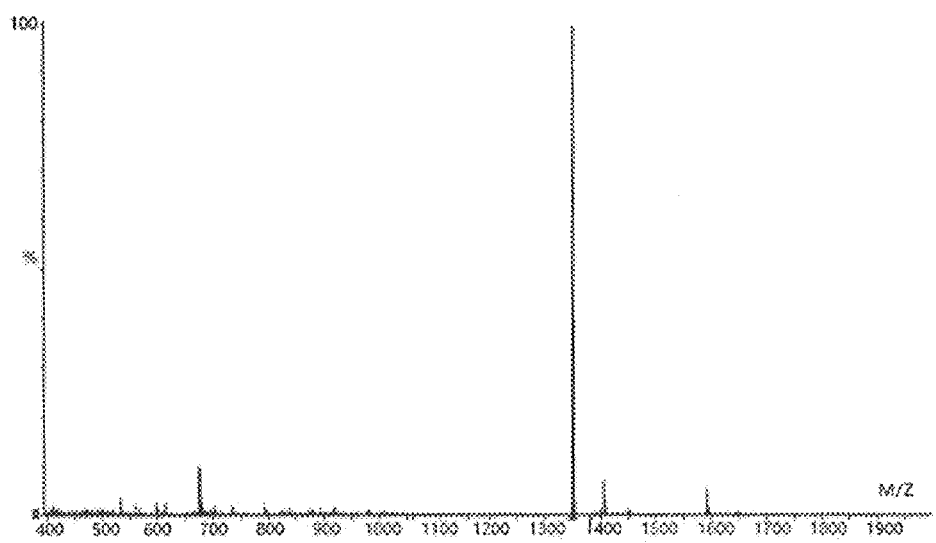
FIG. 2: Mass spectrum identification chromatogram of chemical synthesized cyclo-heptapeptide MRK

RP-HPLC purification is carried out with $C_{18}$ column, the purity of the product is greater than 99% (FIG. 1). Structural confirmation is performed by mass spectrometry and amino acid composition analysis, with a molecular weight of 1346.5 (FIG. 2).

Example 2: Preparation of Chemosynthetic Cyclo-Hepta Modified Peptide MRG by Solid-Phase Synthesis 1. Synthetic Peptide Sequence: $CH_3(CH_2)_{10}CO$-G-(CQHwWHWYC)—RRR—$NH_2$ (Molecular Weight 2055.08)

2. Synthesis Steps:

Step 1, Synthesis of 2 mmol MRG. Rink Amide-AM Resin is selected, and the substitution degree is 0.45 mmol/g. According to the formula, the amount of blank resin=the molar amount of synthesized MRG/the substitution degree of blank resin, that is, the amount of blank resin Rink Amide-AM Resin needed to be weighed=2 mmol/0.45 mmol/g=4.5 g. The weighed blank resin is put into the reaction column and swollen for about 30 min in a mixed solution of N,N-dimethyl formamide and dichloromethane (DMF/DCM=2/1), and then washed with N,N-dimethyl formamide (DMF) as washing solution for 3 times.

Step 2, the protective group Fmoc is removed from the washed resin by de-protection solution, specifically comprising: 20% of the de-protection solution (Vpiperidin/VDMF=20%) is prepared and added to the swollen blank resin in step 1, and then nitrogen is blown for reaction. The Fmoc protective group is removed at two times, 5 min and 15 min respectively, ensuring the complete de-protection. After the de-protection is completed, indene detection reagent is used:

(a) anhydrous ethanol solution of 5% ninhydrin (w/v)
(b) phenol: anhydrous ethanol solution (4:1, w/v)
(c) pyridine Two droplets of each test reagent is added, heated for 3 minutes at a temperature of 105° C. If the color is blue, the protective solution can be pumped out. If no color is showed, de-protection is not complete, the reason should be found out immediately, and de-protection needs to be carried out again. Fmoc-Arg (pbf)-OH and condensation reagents 1-hydroxybenzotriazole (HOBT) and N,N'-diisopropyl carbon diimine (DIC) are used for coupling reaction after washing with DMF for six times. The reaction time is 2-3 h. After the reaction is finished, the colour development reaction experiment of ninhydrin is used to detect whether the reaction is complete, namely a small amount of resin is taken and two droplets of each of the three solutions are heated for 3 min at a temperature of 105° C. If the color is colorless, the reaction is complete. On the contrary, the reaction is incomplete, raw material is supplemented or repeatedly fed until the reaction is complete. The amino acid in the peptide sequence is coupled at one time according to the method described above to obtain:

Gly-Cys(Trt)-Gln(Trt)-His(Trt)-D-Trp(Boc)-Trp(Boc)-His(Trt)-Trp(Boc)-Tyr(tBu)-Cys(Trt)-Arg(pbp-Arg(pbf)-Arg(pbf)-Rink Amide-AM Resin Step 3, after the peptide sequence in step 2 is coupled to Gly, the last group, namely dodecanoic acid (lauric acid), should be coupled when the protective group is removed. It should be noted that dodecanoic acid (lauric acid) is coupled while the coupling, washing, deprotection and detection time are the same. The condensation reagents are benzotriazole-N,N,N',N'-tetramethyl-uronium-hexafluorophosphate (HBTU) and N,N-diisopropyl ethylamine (DIPEA), the reaction time is about one hour. After the reaction is completed, the same method as above is used to determine whether the reaction is complete. Under the condition of complete reaction, the resin is washed with DMF for 3-4 times and the resin is shrunk with methanol (MeOH) for 2 times, shrinking at each time lasts for 10 min. Then the resin is vacuumized to quicksand state to obtain the linear peptide resin of the target peptide:

$CH_3(CH_2)_{10}CO$-Gly-Cys(Trt)-Gln(Tr)-His(Trt)-D-Trp(Boc)-Trp(Boc)-His(Trt)-Trp(Boc)-Tyr(tBu)-Cys(Trt)-Arg(pbf)-Arg(pbf)-Arg(pbf)-RinkAmide-AM Resin Step 4, 8.2 g quicksand peptide resin in step 3 is weighed. Firstly, 100 mL conventional cracking reagent is prepared according to the ratio of TFA:phenyl sulfide:EDT:anisole=90:5:3:2. 8-10 mL cracking reagent is added for every 1 g peptide resin for cracking reaction after shaking well, so that about 70 mL cracking reagent is taken from 100 mL conventional cracking reagent for cracking reaction, the reaction time is about 2-3 h. 60 mL filtrate (partially being lost) is obtained by filtering the resin after the reaction is completed. The filtrate is slowly added to anhydrous ether according to a sedimentation ratio of filtrate to anhydrous ether being 1:6, subjected to standing for 30 min and then settled fully, centrifuged, washed and dried to obtain linear crude peptide: $CH_3(CH_2)_{10}CO$-Gly-Cys-Gln-His-D-Trp-Trp-His-Trp-Tyr-Arg-Cys-Arg-Arg-$NH_2$. After drying, the crude peptide is about 3.6 g.

Step 5, the linear crude peptide obtained in step 4 is grinded to powder, and the linear crude peptide of MRG is dissolved to concentration of 1 mmol/500 mL with the mixed solution of pure water and acetonitrile (V water: V acetonitrile=2:1). The linear crude peptide solution is 1000 mL, and the sample is analyzed by HPLC to locate the appearance time.

Step 6, diluted ammonia is dropwisely added into the linear crude peptide solution in step 5 to make the pH value of the solution range from 7.1 to 7.3 and then 30% hydrogen peroxide diluted by about 10 times is slowly dropwisely added to the solution, wherein the ratio of 30% hydrogen peroxide(usually the 30% hydrogen peroxide is diluted before slowly adding) to the solution is 1 mmol:0.3 mL. After adding hydrogen peroxide, the temperature can be controlled at 30° C. for cyclization. In the process of cyclization, HPLC analysis is needed to trace whether the cyclization is complete or not, and whether the cyclization is carried out mainly according to the linear peptide detected by HPLC analysis and the shifting of cyclized peptide. The cyclization time is about 20-40 min. After the cyclization experiment is completed, the pH of acetic acid solution is adjusted to 4.5 and the cyclization is terminated. The objective crude product is obtained:

$CH_3(CH_2)_{10}CO$-Gly-Cyclo(Cys-Gln-His-D-Trp-Trp-His-Trp-Tyr-Cys)-Arg-Arg-Arg-$NH_2$.

Step 7, the objective crude peptide obtained in step 6 after complete cyclization analyzed by HPLC is separated and purified by preparative $C_{18}$ reversed-phase high performance liquid chromatography (HPLC). The crude peptide is subjected to rotary evaporateion and freeze-drying to obtain fine product. The main steps are as follows:

The crude peptide solution after cyclization crude filtration is filtered through 0.45 mum microporous membrane passing integrity test. After the filtration is completed, the solution is adjusted to the acidic pH for purification.

DIONEX U3000 high performance liquid chromatography is used for process of preparative HPLC separation and purification. An analytical column $C_{18}$, 5 μm, 300 Å, 4.6*250 mm is used; the analysis conditions are as follows: the mobile phase includes A phase of 1% TFA, and B phase of acetonitrile. The preparative instrument is an innovative 5 cm preparative HPLC; the preparative chromatographic column is $C_{18}$, 10 μm, 100 Å. 150*250 mm reversed phase silica gel column.

The filtered crude solution is loaded by a preparative HPLC, injected in a 5 cm chromatographic column. The mobile phase includes: A phase is TFA (1 mL TFA is added to 1000 mL water), B phase is 100% acetonitrile.

Detection wavelength: lambda=230 nm; column temperature: room temperature; samples are collected by clean triangular flasks, the purified solution with the purity of higher than 98% and any individual impurity of less than 1% is qualified. Otherwise, the unqualified sample repeats the above steps, the solution is completely processed, the qualified and unqualified classified purified solutions are obtained, and the above steps are repeated for secondary purification of the unqualified sample to get more qualified samples as far as possible, and then rotary evaporation concentration is carried out.

Step 8, the subpackaged concentrated liquid is freeze-dried to obtain white powder, namely the finished product.

1) The concentrated sample solution is pre-frozen firstly, that is the sample is placed on the partition of freeze-drying box to be pre-frozen. The temperature of the product drops to −40° C. or below, and is kept for about 120 min.

2) Sublimation drying is carried out: the temperature of electric heating is set to 0° C., deviation time is 1 min, the process is kept for about 40 min.

The temperature of the electric heating is set to 10° C. and the deviation time is 500 min.

The temperature of the electric heating is set to 35° C. and the deviation time is 420 min.

3) Desorption: The temperature rises to about 33° C. and is kept for about 240 min. Step 9, purity identification and structure determination of chemosynthetic cyclo-hepta modified peptide MRG.

Figure 3:
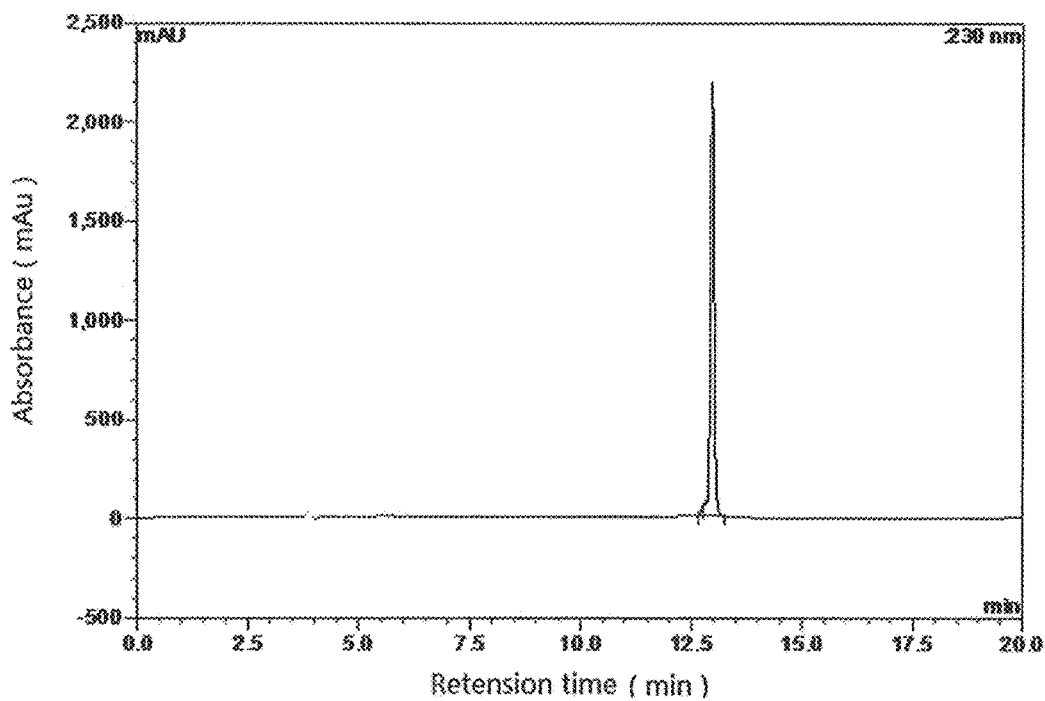
FIG. 3: HPLC purity identification chromatogram of chemosynthetic cyclo-hepta modified peptide MRG
Figure 4:
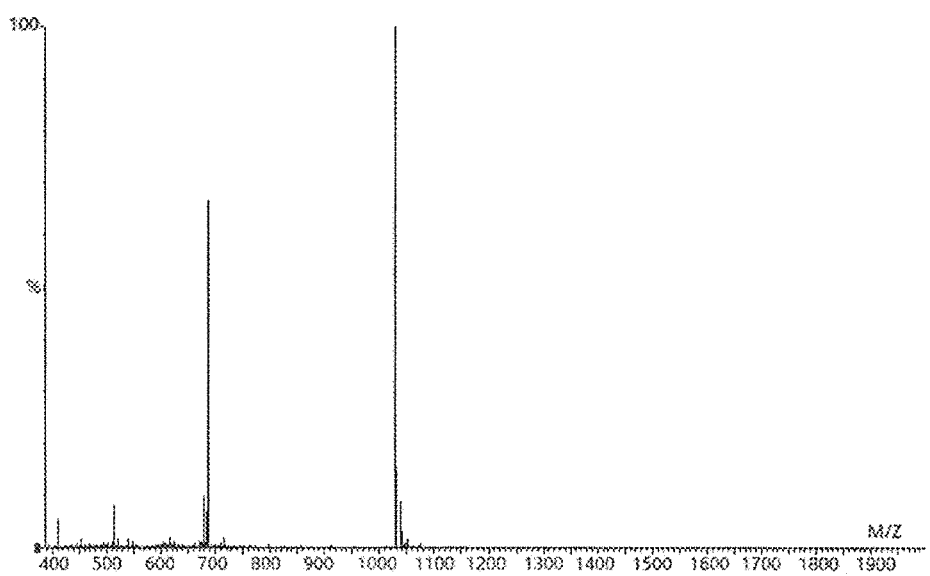
FIG. 4: Mass spectrometric identification chromatogram of chemosynthetic cyclo-hepta modified peptide MRG

The small peptide obtained by chemical synthesis is identified by HPLC and its purity is higher than 95% (FIG. 3). The molecular weight is identified as 2055.08 (1028.54× 2−2) by mass spectrometry (FIG. 4).

Example 3: Comparison of Water Solubility of Chemosynthetic Cyclo-Heptapeptide MRK and Water Solubility of Cyclo-Hepta Modified Peptide MRG Three parts of chemosynthetic cyclo-heptapeptide (MRK) are weighted, 1 mg for each part, and added into 1 mL centrifugal tube, each part is added with 1 mL water for injection, normal saline and dimethyl sulfoxide (DMSO). The results show that chemosynthetic cyclo-heptapeptide (MRK) is insoluble in water or normal saline, and only soluble in DMSO. The solubility of cyclo-heptapeptide MRK in water for injection or normal saline is less than 0.1 mg/mL. The same method is used to detect cyclo-hepta modified peptide MRG. The results show that cyclo-hepta modified peptide MRG is soluble in water for injection, normal saline and DMSO. Through calculation, the solubility of the cyclo-hepta modified peptide in water for injection or normal saline is greater than 1mg/mL. The results show that the water solubility of cyclo-heptapeptide MRG is much better than that of cyclo-heptapeptide MRK.

In order to compare the difference of water solubility between the chemosynthetic cyclo-heptapeptide MRK and cyclo-hepta modified peptide MRG. The inventor scaleed up the synthesis process and makes gradual transition from small-scale to pilot-scale production, making the preparation conditions more stable, and the prepared cyclo-hepta modified peptide MRG once again verifies the water solubility. The results show that the solubility of cyclo-heptapeptide MRK is less than 0.1 mg/mL in water for injection or normal saline, but a greater amount of cyclo-hepta modified peptide MRG, specifically 10 mg, is mixed with 1 mL water for injection or normal saline, all MRG is dissolved and no precipitation is found by standing. The results of multiple experiments are the same. Calculated in percent concentration, the solubility of cyclo-hepta modified peptide MRG in water for injection or normal saline is greater than 1.0%, which completely solves the technical problem that the original cyclo-heptapeptide MRK is insoluble in water.

Example 4: Inhibitory Effect of Chemosynthetic Cyclo-Heptapeptide MRK and Cyclo-Hepta Modified Peptide MRG on the Production of the Toxins of *Staphylococcus aureus*

1. Experimental Reagents, Consumables and Instruments

The chemosynthetic cyclo-heptapeptide MRK (CQHWWHWYC, SEQ ID NO: 1) and the chemosynthetic cyclo-hepta modified peptide MRG ($CH_3(CH_2)_{10}CO$-G-(CQHwWHWYC)—RRR—$NH_2$) are synthesized by ChinaTech Peptide (Suzhou) Co., Ltd. The purity is greater than 95%. *Staphylococcus aureus* 04018 strain is preserved by the Laboratory of Biochemistry and Molecular Biology, Institute of Basic Medical Sciences, Academy of Military Medical Sciences. Blood plate (fresh blood agar culture board) is from Beijing Aoboxing Bio-tech Co. Ltd. BHI plate is made by our laboratory. Imported BHI (Bacto™ Brain Heart Infusin) is purchased from the BD Company, USA. DMEM medium is purchased from CIBCO, USA. Imported fetal cow serum is purchased from the PAN BIOTECH Company, USA. 0.22 μm membrane is purchased from PALL Corporation, USA. MDBK cells are preserved in the cell bank of our laboratory. Desktop centrifuge is from EPPDORF Company, Germany. Enzyme linkage is from MICROPLATE, USA. Cell culture bottles are purchased from CORNING, USA. Centrifugal tubes, graduated pipette, capillary burette and disposable syringes and other consumables are from our laboratory.

2. Experimental Methods

For the determination method for inhibitory level on the toxins of *Staphylococcus aureus*, please refer to literatures. (Yang G, et al. A novel peptide screened by phage display can mimic TRAP antigen epitope against *Staphylococcus aureus* infections. J Biol. Chem. 2005, 280: 27431-27435), details are as follows:

1) *Staphylococcus aureus* strain 04018 frozen in refrigerator is scribbed to a blood plate or BHI plate; cultured in an incubator for 16 hours until monoclonal colony is observed in the plate, and placed in a 4° C. refrigerator for standby use.

2) After 8 hours, the monoclonal colony in the plate is randomly selected, 25 mL test tubes of the BHI medium is inoculated with the monoclonal colony; and then the two test tubes are shook in a shaking table at a temperature of 37° C. at a speed of 200 rpm, the bacteria are collected after 16 hours, the bacteria solution in the two test tubes are mixed evenly for standby use.

3) The chemosynthetic peptide MRK and MRG and the positive control (the toxins of Staphylococcus aureus inhibitor protein TP) are dissolved in normal saline, diluted to different concentrations, and added to bacteria BHI medium. The final concentrations of small peptides are 0, 1.5, 5, 15, 50, 150 and 500 μg/mL respectively. The solvent control is the same amount of normal saline; the negative control is the BHI medium of Staphylococcus aureus; and a normal cell control is also provided.

4) The chemosynthetic peptides of different concentrations are co-incubated with Staphylococcus aureus 04018 and cultured for 6 hours, and then bacteria are collected. 700 μL bacterial suspensions are added to EP tubes, centrifuged at 8000 rpm for 5 min, supernatants are obtained, boiled at a temperature of 100° C. for 7 min, and centrifuged at a speed of 14000 rpm for 10 min. 10 μL supernatants are taken, added into a 96-microwell cell culture plate inoculated with 1×10<5>/mL MDBK cells. After continuous culture for 18-20 hours, 5 μL MTT solution (5 mg/mL) is added to each microwell, 100 μL 10% SDS+0.01M HCl solution is added to each microwell after 3 hours. After culture in the incubator at a temperature of 37° C. for 20 hours, detection at 595 nm and reading are carried out by an enzyme-linked immunometricmeter.

3. Experimental Results and Conclusions

The experimental results show that the chemosynthetic cyclo-hepta modified peptide MRG prepared by the example of the invention can be dissolved in the normal saline. The chemosynthetic peptide may inhibit the production of the toxins of Staphylococcus aureusand has an obvious protective effect on the proliferation inhibition of MDBK cells induced by the toxins of Staphylococcus aureus, showing a certain dose-effect relationship. The inhibitory effect of 5 μg/mL small peptide (g/mL) on the production of the toxins of Staphylococcus aureus is greater than that of TP protein (positive control), but the chemosynthetic cyclo-heptapeptide MRK is insoluble in water, and its suspension could not inhibit the production of the toxins of Staphylococcus aureus (Table 1 below is an observation on the inhibitory effect of chemosynthetic cyclo-heptapeptide MRK and cyclo-hepta modified peptide MRG on the production of the toxins of Staphylococcus aureus). This difference in antimicrobial activity is considered by the inventors to be the result of solubility improvements and structural changes in cyclo-hepta modified peptide, rather than simple changes in solubility.

TABLE 1

Inhibitory effect of chemosynthetic peptide on production of the toxins of Staphylococcus aureus

| Group (dose) | MDBK cell OD (M ± SD) | Cell survival (%) |
| --- | --- | --- |
| MRG (0.15 mg/mL) | 0.473 ± 0.004 | 96 |
| MRG (0.05 mg/mL) | 0.454 ± 0.015 | 92 |
| MRG (0.005 mg/mL) | 0.296 ± 0.001 | 60 |
| MRK (0.15 mg/mL) | 0.171 ± 0.001 | 35 |
| MRK (0.05 mg/mL) | 0.098 ± 0.014 | 20 |
| MRK (0.005 mg/mL) | 0.123 ± 0.011 | 25 |

TABLE 1-continued

Inhibitory effect of chemosynthetic peptide on production of the toxins of Staphylococcus aureus

| Group (dose) | MDBK cell OD (M ± SD) | Cell survival (%) |
| --- | --- | --- |
| TP positive control (1 mg/mL) | 0.464 ± 0.028 | 94 |
| normal saline control | 0.133 ± 0.008 | 27 |
| Staphylococcus aureus negative control | 0.112 ± 0.030 | 23 |
| BHI medium control | 0.494 ± 0.017 | 100 |

Example 5: Therapeutic Effect of Chemosynthetic Cyclo-Hepta Modified Peptide MRG on Bacteremia Induced by Staphylococcus aureus Infection in Mice 1. Experimental Reagents, Consumables and Instruments The chemosynthetic cyclo-hepta modified peptide MRG ($CH_3(CH_2)_{10}CO$-G-(CQHwWHWYC)—RRR—$NH_2$) is synthesized by ChinaTech Peptide (Suzhou) Co., Ltd. The purity is greater than 95%. Staphylococcus aureus Newman strain is preserved by the Institute of Basic Medical Sciences, Academy of Military Medical Sciences. Blood plate (fresh blood agar culture board) is from Beijing Aoboxing Bio-tech Co., Ltd. BHI plate is made by our laboratory. Imported BHI (Bacto™ Brain Heart Infusin) is purchased from the BD Company, USA. Sodium pentobarbital is purchased from Sigma Corporation, USA. The table top centrifuge is form EPPDORF Company, Germany. Centrifugal tubes, graduated pipette, and disposable syringes and other consumables are from our laboratory. 2. Experimental methods 1) Preparation of Staphylococcus aureus Newman Solution Newman monoclonal strain with hemolytic circles is selected, 3 mL BHI medium is inoculated with the strain, and the strain is shook overnight at a speed of 220 rpm and a temperature of 37° C.

1 mL overnight strain is centrifuged at a speed of 5000 rpm for 2 min, and the supernatant is removed.

20 mL aseptic PBS is added for resuspension at a speed of 5000 rpm for 5 min, and the supernatant is removed.

5 mL aseptic PBS resuspended bacteria is diluted to OD600=0. 2.

2) Establishment of Model of Bacteremia and Determination of Polypeptide Activity in BALB/c Mice BALB/c mice (female, 8 weeks) are subjected to intraperitoneal injection of anesthetic (1% pentobarbital) (200 μL for each mouse).

Newman solution (OD600=0.2, 100 μL for each mouse) is injected into retrobulbar venous plexus.

After 30 minutes of infection, 6 mice are injected with polypeptide at enterocoelia (0.5 mg/mL, 200 μL for each mouse) and 7 mice in control are injected with sterile water (200 μL for each mouse).

The times of the mouse in one week are recorded and used for drawing survival curves.

3. Experimental Results and Conclusions

Figure 5:
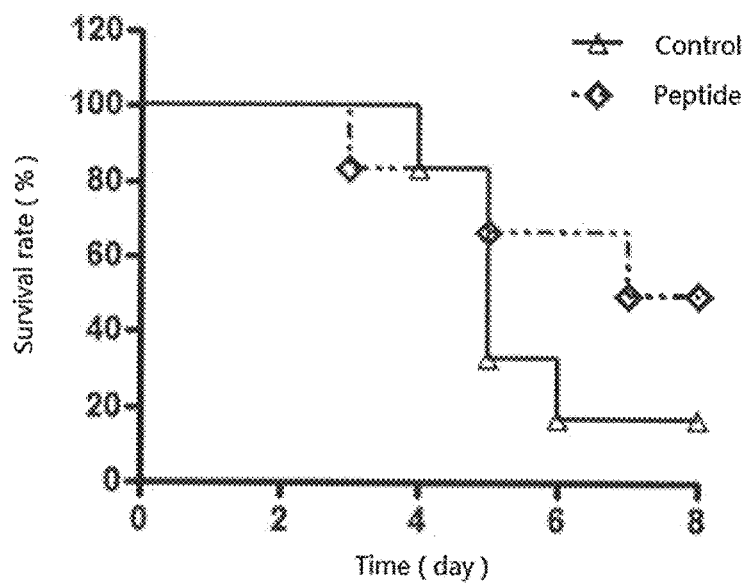
FIG. 5: Therapeutic effect of the chemosynthetic peptide on bacteremia induced by *Staphylococcus aureus* infection in mice

The experimental results show that the chemosynthetic cyclo-hepta modified peptide MRG prepared by the example of the invention can reduce the death caused by bacteremia in mice induced by Staphylococcus aureus at a dose of 5 mg/kg body weight, and the survival rate is greatly improved compared with the control of aseptic water for injection. The chemosynthetic cyclo-heptapeptide MRK also has a good inhibitory effect on Staphylococcus aureus infection in vivo (FIG. 5).

The invention claimed is:

1. A peptide having the following formula:

$CH_3-(CH_2)m\text{-}CO\text{-}G\text{-}(CQHwWHWYC)\text{-}RRR\text{-}NH_2$;

wherein:

m=3-17;

G represents L-glycine;

C in the (CQHwWHWYC) portion of the peptide represents L-cysteine, Q represents L-glutamine, H in the (CQHwWHWYC) portion of the peptide represents L-histidine, W represents L-tryptophan, w represents D-isomer of tryptophan, Y represents L-tyrosine, R represents L-arginine, and two cysteines represented by C are linked by a disulfide bond.

2. The peptide of claim 1, wherein the peptide binds to the virulence stimulator ribonucleic acid III activating protein (RAP) of *Staphylococcus aureus* and inhibits the production of the toxins of *Staphylococcus aureus*; and wherein the peptide is synthesized by chemical synthesis.

3. The peptide of claim 1, wherein the peptide is obtained by chemical synthesis.

4. The peptide of claim 1, wherein m=6-14.

5. The peptide of claim 1, wherein m=8-12.

6. The peptide of claim 1, wherein $CH_3-(CH_2)m\text{-}$ is $CH_3(CH_2)_{10}\text{-}(m=10)$.

7. A method for treating *Staphylococcus aureus* infection in a subject in need thereof, the method comprising administering a therapeutically effective amount of the peptide of claim 1.

8. The method of claim 7, wherein the subject has a disease caused by *Staphylococcus aureus* infection selected from the group consisting of burn and war wound infection, pneumonia, endocarditis, septicemia, or toxic shock *Staphylococcus aureus* infection.

9. The method of claim 8, wherein the disease caused by *Staphylococcus aureus* infection is pneumonia.

\* \* \* \* \*

UNITED STATES PATENT AND TRADEMARK OFFICE
CERTIFICATE OF CORRECTION

PATENT NO. : 10,905,735 B2
APPLICATION NO. : 16/097964
DATED : February 2, 2021
INVENTOR(S) : Wenhui Xia, Xiaoping Liang and Liangyou Wang Page 1 of 1

It is certified that error appears in the above-identified patent and that said Letters Patent is hereby corrected as shown below:

On the Title Page

Item (12):
Shao et al.

Should read:
Xia et al.

Item (72):
"Ningsheng Shao, Beijing (CN); Guang Yang, Beijing (CN); Liangyou Wang, Suzhou (CN); Hongmei Ding, Beijing(CN); Yaping Gao, Beijing (CN); Shaohua Li, Beijing (CN); Hui Li, Beijing (CN); Jie Li, Beijing (CN); Jie Dong, Beijing (CN); Wenhui Xia, Haikou (CN); Xiaoping Liang, Haikou (CN)"

Are changed to:
--Wenhui Xia, Haikou (CN); Xiaoping Liang, Haikou (CN); Liangyou Wang, Suzhou (CN)--

Signed and Sealed this
Ninth Day of July, 2024

Katherine Kelly Vidal
*Director of the United States Patent and Trademark Office*